United States Patent [19]

Moran

[11] Patent Number: Plant 7,429

[45] Date of Patent: Jan. 22, 1991

[54] BAHIAGRASS PLANT 'B-1'

[76] Inventor: William E. Moran, 1703 Zipperer Rd., Bradenton, Fla. 34202

[21] Appl. No.: 406,433

[22] Filed: Sep. 12, 1989

[51] Int. Cl.[5] ..... A01H 5/00

[52] U.S. Cl. ..... Plt./89

[58] Field of Search ..... Plt./89

*Primary Examiner*—James R. Feyrer

*Attorney, Agent, or Firm*—Fleit, Jacobson, Cohn, Price, Holman & Stern

[57] ABSTRACT

I disclose that my herein invention of a new genotype of Bahiagrass plant was discovered by me in a cultivated pasture at Manatee County, State of Florida. This new discovered Bahiagrass plant is a perennial with a prostrate to decumbent growth habit, exhibits an attractive dark green yellowish color, color 7.5 GY 4/4, has a fast rate of horizontal spread and produces prostrate to decumbent flowering culms.

2 Drawing Sheets

The present invention relates to a new and distinct genotype of Bahiagrass (*Paspalum notatum* Flugge) plant which was discovered by me, growing as a newly found seedling of unknown parentage which originated in a cultivated bahiagrass pasture located in Manatee County in the state of Florida. The pasture was originally seeded to bahiagrass approximately 20 years earlier and has since been overseeded several times with the bahiagrass variety 'Argentine.' I observed that this genotype of bahiagrass was phenotypically different than other bahiagrass plants growing in the pasture by having a more prostrate (dwarf) growth habit, a darker green color and softer leaf texture. It was also expressing a more vigorous laterial growth rate, forming a distinct patch area in the pasture. I removed a sod piece consisting of several tillers and rhizomes from the field, broke them into small vegetative pieces and transplanted them into individual pots designated B-1. I also established several pots of other known varieties of Bahiagrass for comparison with this new genotype. I observed again that the new genotype was more prostrate in growth habit, darker in color, and faster to establish from vegetative propagules when compared to the closest known bahiagrass varieties, common and Argentine. The root systems of the new claimed genotype of bahiagrass, and plants of the closest known varieties, do not show noticeable differences. The new claimed genotype B-1 of bahiagrass produces prostrate to decumbent flowering culms compared to the erect flowering culms of known varieties. Continued asexual reproduction by me, through tillers and rhizomes of this new genotype, have confirmed that the above characteristics are transmitted through succeeding propagations and have confirmed that the above information can be used to distinguish genotype B-1 from other bahiagrass varieties.

A primary objective of the invention is to provide a new and distinct variety of Bariagrass plant having desirable turfgrass characteristics that can be vegatatively propagated. The faster rate of establishment and prostrate growth habit of genotype B-1 suggest its potential benefits as a turfgrass. However, at present, its performance with adequate cultural practices under field conditions is not known.

Figure 1:
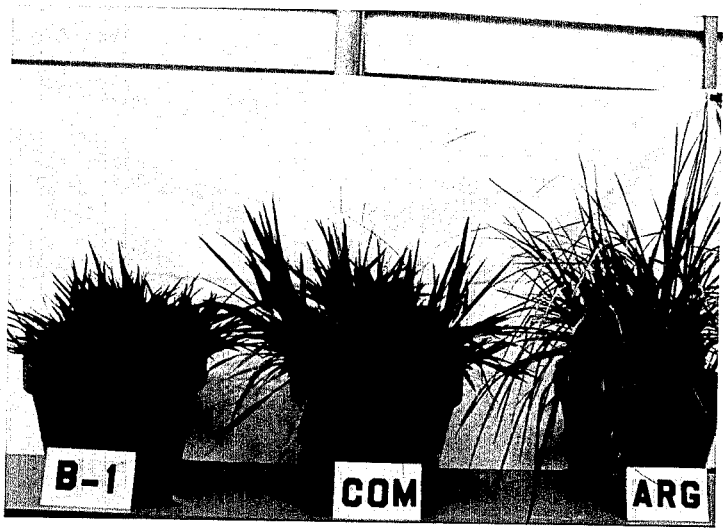
FIG. 1. Is a photograph of the new claimed genotype B-1 and the two nearest known varieties, common and Argentine plants grown for 168 days under the same greenhouse conditions showing the relative plant growth and color. Plants were clipped to a height of 5 cm, 91 days before photograph was taken.
Figure 3:
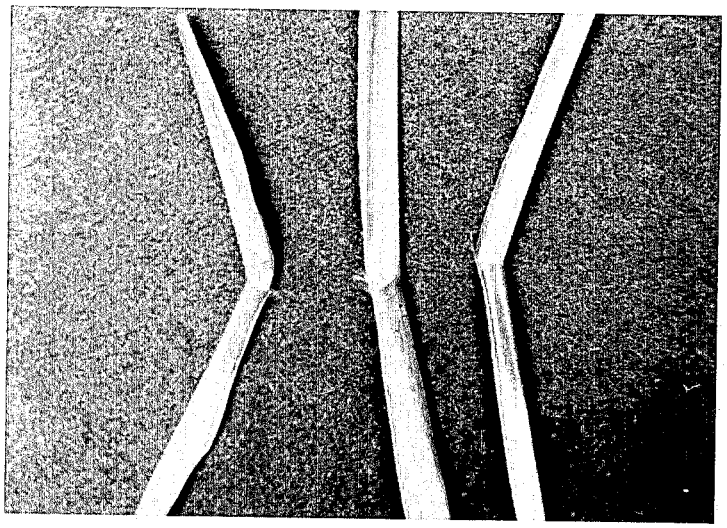
FIG. 3. Is a photograph of the leaf sheath and color area of the new claimed genotype B-1 (left) and the closest known varieties of bahiagrass, common (center) and Argentine (right). The lower margin of the color area on B-1 is covered with short (1–2 mm) soft hairs; villous. The sheath and leaf blade are glabrous. Common bahiagrass has a tuft of longer (6–10 mm) hair on the upper color area and the upper leaf surface has scattered hair (puberulent). Argentine bahiagrass is nearly glabrous with only a few (4 to 6) hair (2–5 mm long) at the upper color area.
Figure 2:
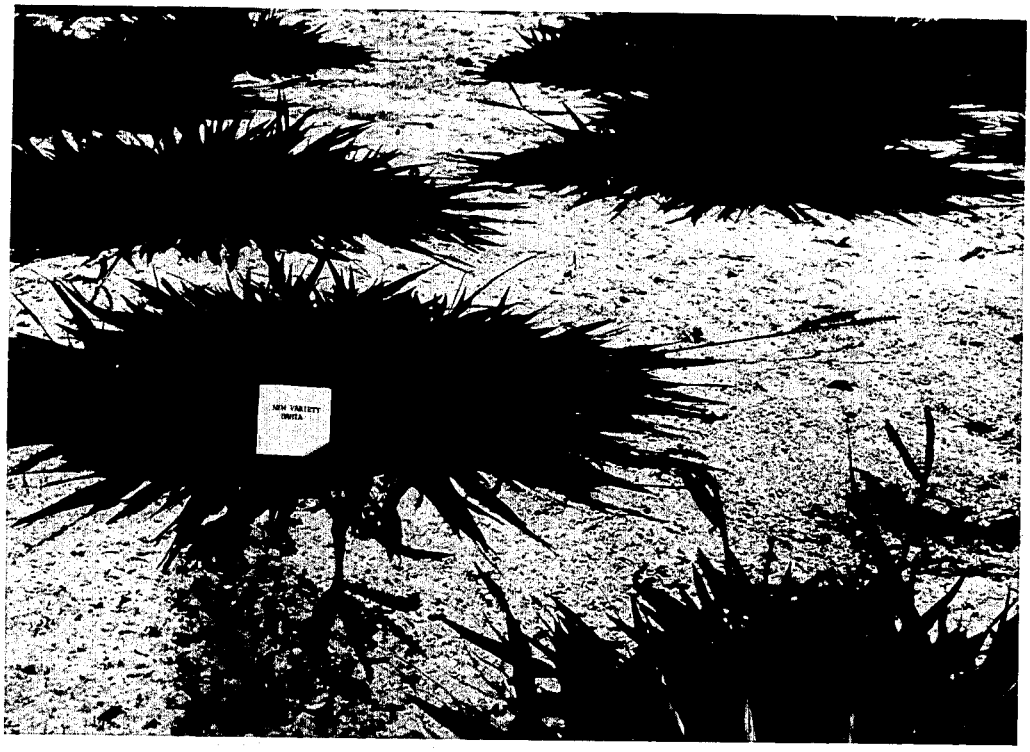
FIG. 2. Is a photograph of bahiagrass B-1 plants growing in a field nursery in Manatee County, Fla., showing the prostrate plant growth habit and prostrate to decumbent flowering culm production of this claimed genotype of bahiagrass.

A detailed description of the new and distinct genotype of bahiagrass plant B-1 is:

(a) An attractive dark green yellowish color designated 7.5 GY 4/4 (Munsell Book of Color).

(b) The growth habit is prostrate or procumbent with a fast horizontal rate of spread from stout rhizomes.

(c) Leaves are folded in bud. Mature leaf blades are flat to slightly folded inward.

(d) The first mature leaf is $7.6 \pm 0.6$ mm in width and $13.1 \pm 2.9$ cm long.

(e) Culms are compressed, $15.5 \pm 2.3$ cm tall.

(f) Auricles and ligule are absent.

(g) Plants are glabrous except for villous hair (1–2 mm long) on the lower margin of the color area.

(h) Flowering culms are prostrate to decumbent with 2 or 3 recemes.

A detailed description of the closest known variety of bahiagrass plant, which is known as common, is:

(a) A medium green yellowish color designated 7.5 GY 5/6 (Munsell Book of Color).

(b) the growth habit is decumbent to semi-erect with a medium horizontal open rate of spread from short, stout, woody rhizomes.

(c) Leaves are folded in bud. Mature leaf blades are folded inward to form 120° to 140° angles.

(d) The first mature leaf is 10.5±0.9±mm in width and 22.2±3.1 cm long.

(e) Culms are semi-erect; 31.1±7.2 tall.

(f) Auricles and ligule are absent.

(g) Puberulent hair on upper leaf surface and a tuft of long (6–10 mm) hair on the upper color area.

(h) Flowering culms are erect with 2 or 3 recemes, rarely to 5.

A detailed description of the closest known variety of bariagrass grass plant, which is known as Argentine, is:

(a) A yellowish green color designated 7.5 GY 6/8 (Munsell Book of Color).

(b) The growth habit is semi-erect to decumbent with a slow horizontal open rate of spread from short, stout, woody rhizomes.

(c) Leaves are folded in bud. Mature leaf blades are elongated and folded inward to form 90° to 110° angles.

(d) The first mature leaf is 6.3±0.8 mm in width and 40.2±8.1 cm long.

(e) Culms are erect; 50.0±6.2 cm tall.

(f) Auricles and ligule are absent.

(g) Plants are glabrous except for 4 to 6 hair (2–5 mm long) at the upper color area.

(h) Flowering culms are erect with 2 or 3 recemes, rarely to 5.

Having thus disclosed my discovery, I claim:

1. A new and distinct genotype of bahiagrass plant, B-1, substantially as herein described and illustrated, characterized particularly as being prostrate to decumbent (dwarf) in growth habit, faster rate of lateral spread, attractive dark green yellowish color designated 7.5 GY 4/4 and producing prostrate to decumbent flowering culms.

* * * * *